United States Patent [19]

Bull et al.

[11] Patent Number: 5,266,899
[45] Date of Patent: Nov. 30, 1993

[54] SALT ANALYZER SWITCHABLY CAPABLE OF EMPLOYING CONTACT AND NON-CONTACT CONDUCTIVITY PROBES

[75] Inventors: Rame W. Bull, Mount Prospect; Richard T. Prince, River Forest, both of Ill.

[73] Assignee: Akzo N.V., Arnhem, Netherlands

[21] Appl. No.: 830,022

[22] Filed: Jan. 31, 1992

[51] Int. Cl.$^5$ .............................. G01N 27/07
[52] U.S. Cl. ........................... 324/439; 324/115; 324/130; 324/609; 324/445; 324/446
[58] Field of Search ............ 324/439, 442, 204, 445, 324/444, 115, 130, 609, 446

[56] References Cited

U.S. PATENT DOCUMENTS

| | | | |
|---|---|---|---|
| 2,542,057 | 4/1928 | Relis | 175/183 |
| 3,495,164 | 2/1970 | Dauphinee | 324/442 |
| 3,710,811 | 1/1973 | Leverenz et al. | 137/5 |
| 3,806,798 | 4/1974 | Gross | 324/30 |
| 3,827,450 | 8/1974 | Leverenz et al. | 137/88 |
| 3,867,688 | 2/1975 | Koski | 324/30 |
| 3,906,353 | 9/1975 | Murdock | 324/442 |
| 3,924,175 | 12/1975 | Wilson | 324/30 |
| 3,979,655 | 9/1976 | Ebling et al. | 324/30 |
| 4,066,948 | 1/1978 | Hawk et al. | 324/442 |
| 4,190,827 | 2/1980 | Diamond | 324/439 |
| 4,220,920 | 9/1980 | Gross | 324/442 |
| 4,227,151 | 10/1980 | Ellis et al. | 344/448 |
| 4,331,923 | 5/1982 | Akers, Jr. | 324/442 |
| 4,511,845 | 4/1985 | Dauphinee et al. | 324/444 |
| 4,740,755 | 4/1988 | Ogawa | 324/445 |
| 4,751,466 | 6/1988 | Colvin et al. | 324/449 |
| 4,767,995 | 8/1988 | Berry, Jr. | 324/447 |
| 4,823,087 | 4/1989 | Sugimori | 324/441 |
| 4,825,168 | 4/1989 | Ogawa et al. | 324/439 |
| 4,833,413 | 5/1989 | Head | 324/449 |

FOREIGN PATENT DOCUMENTS

0426012A2  5/1991  European Pat. Off.
WO9106000  5/1991  PCT Int'l Appl.

Primary Examiner—Kenneth A. Wieder
Assistant Examiner—Jose M. Solis
Attorney, Agent, or Firm—Ralph J. Mancini; Louis A. Morris

[57] ABSTRACT

A salt analyzer is disclosed capable of measuring the conductivity of a saline solution when either contact or non-contact probes are used. In particular, the salt analyzer employs circuitry capable of switchably measuring the various electrical parameters necessary for determining the conductivity of a solution when either contact or non contact probes are used.

6 Claims, 1 Drawing Sheet

SALT ANALYZER SWITCHABLY CAPABLE OF EMPLOYING CONTACT AND NON-CONTACT CONDUCTIVITY PROBES

BACKGROUND OF THE INVENTION

The current invention relates to a salt analyzer, and more particularly to a salt analyzer switchably capable of use with both contact and non-contact conductivity probes.

The salinity of a solution is related to the electric conductivity of the solution. Consequently, the salinity or ion concentration of a solution may be determined by measuring the electric conductivity of the solution with devices known generally as salimeters or salt analyzers. These devices basically are comprised of an exciting AC voltage source, a pair of electrodes, and a circuit capable of measuring a current or voltage induced in the solution due to the exciting AC voltage. The pair of electrodes is either constituted in the form of a probe capable of being immersed directly into a solution or provided in a measuring cell into which the solution is sampled. The exciting AC voltage source supplies an AC voltage between the electrodes with the probe immersed in solution or with the solution sampled into a cell. In principle, the solution conductivity (and thus its ion concentration) is obtained from the data of voltage and current between the electrodes and the geometry of the pair of electrodes. The device is typically designed to give a resultant value of the conductivity and/or salinity of the solution based on the probe or cell constant reflecting the geometry of the pair of electrodes.

Generally the electrodes used with salt analyzers are one of two types. The first type is referred to as a "contact" probe, cell or sensor. With a contact probe conductivity of a solution is determined by measuring the current through the cell for a given voltage applied then multiplying by the cell constant appropriate for the cell geometry. As known by the skilled artisan, the cell constant is (electrode separation)/(cell cross-sectional area).) The second general type of sensing electrode is the "contactless" or "non-contact" probe, sensor or cell.

In it simplest form, a non-contact probe consists of two toroidal coils complied by a loop of the solution being tested. The non-contact probe operates by applying a voltage to the first coil, measuring the induced secondary voltage in the other coil and multiplying by the appropriate cell constant.

Salt analyzers capable of employing either contact probes or non-contact probes are well-known in the art. In particular, the art focuses on refinements to overcome various technical problems recurrent with either contact or non-contact probes or to improve the operation of such probes. For example, U.S. Pat. No. 4,227,151 discloses a contact-type electrical measuring cell comprising at least four (4) concentric circular electrodes separated by annular areas and adapted to receive a temperature sensitive element. As part of the disclosure of U.S. Pat. No. 4,227,151 a single electrical system is taught to measure the conductivity of both the "measured liquor" and the "reference liquor" by employing suitable switching means. In U.S. Pat. No. 3,979,665 a conductivity monitoring system having a temperature compensation means and an arrangement for indicating failure of that compensating means is disclosed. Improvements to non-contact probe systems are disclosed, inter alia, in U.S. Pat. No. 4,825,168 which teaches the use of a square wave excitation signal in the drive transformer and in WO 91/0600 which teaches a non-contact measuring cell having three toroids with a switching control to allow conversion to a conventional two toroid system or to change the drive and sensing toroids.

Each type of probe, contact and non-contact, has its own limitations and advantages. A contact probe is prone to contamination at the electrode surface, requiring periodic cleaning and, therefore, presenting a maintenance problem in e.g. pipeline installations. A contact probe can also experience electrode-to-liquid interface impedance introducing errors when measuring low resistance (high conductivity) solutions. However, a contact probe is particularly useful in laboratory scale bench-top applications due to its relative independence from the container holding the tested solution.

A non-contact probe is less sensitive to coating and surface contamination, requiring less maintenance than a contact probe. This makes such probes better suited to applications having difficult accessibility. On the other hand, since all the liquid surrounding a non-contact probe forms part of the conductive path, the effective geometry is not as well defined as that of a contact probe. Consequently use of a non-contact probe as a "dip-in" probe is problematic since the depth of submersion will affect the measurement. Additionally, errors will be introduced if the conductive path is distorted by the container bottom or walls.

Clearly, employment of contact probes or non-contact probes changes from application to application and environment to environment. However, current salt analyzers are dedicated to either contact or non-contact probes since, at their most basic level, contact probes detect current and non-contact probes detect induced voltage. The current invention provides, among other things, a salt analyzer capable of use with both contact and non contact probes.

SUMMARY OF THE INVENTION

In its primary embodiment, the current invention is directed to a salt analyzer for detecting the salinity of a liquid solution in a cell by measuring the electric conductivity of said liquid solution by employing a probe immersed in said liquid solution, said salt analyzer switchably capable of using both contact conductivity probes and non-contact conductivity probes, said salt analyzer comprising an AC voltage source for supplying an exciting AC power necessary to measure the conductivity of a liquid solution whose salinity is to be detected; said AC voltage source being provided with an output voltage adjusting means; a first voltage amplifying means for outputting a voltage proportional to the voltage across the cell when a contact probe is used and the induced voltage when a non-contact probe is used; an amplifying means capable of outputting a second voltage corresponding to the current in the cell as its function when a contact probe is used or proportional to the drive voltage as its function when a non-contact probe is use; and a switching means associated with said contact and non-contact probes capable of changing the function of said amplifying means depending on whether a contact or non-contact probe is used.

DETAILED DESCRIPTION OF THE INVENTION

Figure 1:
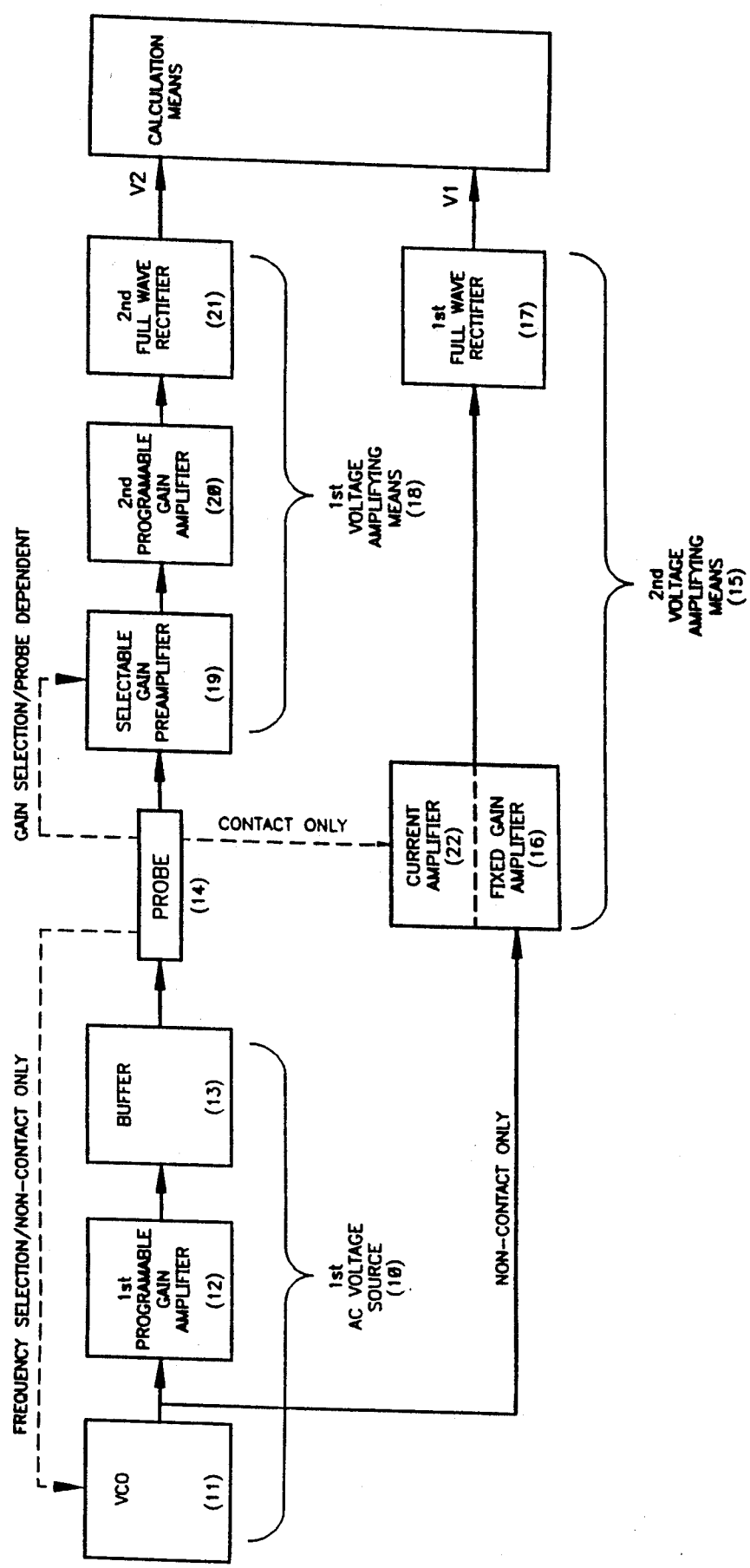
FIG. 1 is a block diagram of the circuit for the salt analyzer of the current invention.

Referring to FIG. 1, AC voltage source 10 supplies the drive frequency for the salt analyzer. In FIG. 1, AC voltage source 10 is comprised of voltage controlled oscillator 11, first programmable gain amplifier 12 and buffer 13. The output of voltage controlled oscillator 11 is fed into first programmable gain amplifier 12. The output of first programmable gain amplifier 12 is fed into buffer 13, the output of which provides the power to drive probe 14.

If a non-contact probe is employed the voltage controlled oscillator 11 output is also fed into second voltage amplifying means 15 to obtain voltage 1 (V1). In FIG. 1, second voltage amplifying means 15 is comprised of fixed gain amplifier 16 and first full wave rectifier 17. The output of fixed gain amplifier 16 is fed into first full wave rectifier 17. The output of first full wave rectifier 17 is V1.

The first voltage amplifying means 18 is comprised of selectable gain preamplifier 19, second programmable gain amplifier 20 and second full wave rectifier 21. The first voltage amplifying means 18 is switchably connected depending on the probe type employed. If a non-contact probe is used, the sense winding (secondary contact) is connected to selectable gain preamplifier 19. If a contact probe is used, the selectable gain preamplifier 19 is connected across the probe terminals. Irrespective of the probe type used, the output of selectable gain preamplifier 19 is fed to second programmable gain amplifier 20. The output of second programmable gain amplifier 20 drives a second full wave rectifier 21 to obtain voltage 2 (V2).

If a contact probe is employed, the current in the cell must also be determined and converted to corresponding voltage. Therefore, when probe 14 is a contact probe, contact probe 14 will be switchably connected to current amplifying means 22 to provide current flow through such means. By wiring configuration, second voltage amplifying means 15 may be used to measure the voltage (V1) corresponding to the current through probe 14 when contact probes are employed.

In operation the drive frequency of the current salt analyzer is determined by voltage controlled oscillator 11. The drive frequency for non-contact probe configuration is typically 5.8 KHz and for contact probe configuration approximately 12 KHz. The appropriate frequency may be selected by wiring each probe connection to adjust the voltage controllable oscillator 11 to the desired frequency when the probe is connected to the salt analyzer. The output of voltage controllable oscillator 11 is fed into first programmable gain amplifier 12, typically supplying a gain of 1, 2, 4 or 8 as determined by the requirements of the digital system. As discussed above, for non-contact probe applications, voltage controllable oscillator output 10 is also fed into second voltage amplifying means 15, the output of which is V1 which is sent to the digital calculation portion of the apparatus to determine conductivity.

Further describing a non-contact probe in operation, the secondary or sense winding of the probe 14 is connected to selectable gain preamplifier 19 which typically has a gain of 134. This gain can be adjusted by the wiring of the probe connector.

In the operation of a contact probe, selectable gain preamplifier 19 is adjusted, usually to a gain of one, and selectable gain preamplifier 19 is connected across the probe terminals. The preamplifier 19 output is fed into second programmable gain amplifier 20 with a typical gain of 1, 2, 4 or 8, depending on the requirements of the digital calculation portion of the apparatus. The output of second programmable gain amplifier 20 drives second full wave rectifier 21 producing V2 which is sent to the digital calculation portion of the apparatus to determine conductivity.

As described above, current amplifying means 22 is connected to measure the probe current flow. This current is converted, preferably via second voltage amplifying means 15 to output a voltage V1 corresponding to current flowing through the contact probes.

For both contact probes and non-contact probes, V1 and V2 determined as described above, are fed to a process (typically digital) which will calculate solutions conductivity ($K_T$) based on the formulas $$K_T = \frac{G_S}{G_A} \ \frac{V_1}{V_2} \ C_C \ \text{(milli Siemens/cm)(mS/cm)} \quad \text{Formula I}$$

for contact probes and $$K_T = \frac{500}{G_S G_P} \ \frac{V_2}{V_1} \ C_C \ \text{(mS/cm)} \quad \text{Formula II}$$

for non-contact probes wherein
  $G_P$ = gain of first programmable gain amplifier 12,
  $G_A$ = gain of current amplifier 22, and
  $G_S$ = gain of second programmable gain amplifier 20.
  $C_c$ = cell constant Once conductivity ($K_T$) is determined the salinity may be calculated in accordance with the following steps:
1. Calculate conductivity at a standard temperature (20° C.) in accordance with the formula $$K = K_T/(0.61047 + 1.8409(10^{-2})T + 5.8044(10^{-5})T^2),$$

T = temperature (°C.) of the solution in the cell.
2. Compute salinity
   a. in terms of molar concentration (M, g mol/liter of solution)

$$M = K/(100.0334 - 4.679505(10^{-1})K + 2.82199(10^{-3})K^2 - 8.33981(10^{-6})K^3); \text{ or}$$

b. in terms of concentration by weight (A, g/g of solution)

$$A = K/(17.0753 - 7.12862(10^{-2})K + 4.60875(10^{-4})K^2 - 1.36797(10^{-6})K^3); \text{ or}$$

c. in terms of grams per liter of solution ($C_s$), $$C_s = 58.4428M; \text{ or}$$

d. in terms of salometer degrees (S), $$S = A/0.26395$$

I claim:

1. A salt analyzer for detecting the salinity of a liquid solution by measuring the electrical conductivity of said liquid solution in a cell by employing a probe immersed in said liquid solution, said salt analyzer adaptable for use with either contact conductivity probes or non-contact conductivity probes, said salt analyzer comprising an AC voltage source for supplying an exciting AC power to drive said probe in order to measure the conductivity of a liquid solution whose salinity is to be detected, said AC voltage source being provided with an output voltage adjusting means; a first voltage amplifying means for outputting a first voltage proportional to the voltage across the cell as its function when a contact probe is used or the induced voltage as its function when a non-contact probe is used; a second voltage amplifying means for outputting a second voltage corresponding to the current in the cell as its function when a contact probe is used or proportional to the drive voltage as its function when a non-contact probe is used; and a switching means associated with said contact and non-contact probes capable of changing the function of said first and second voltage amplifying means depending on whether a contact or non-contact probe is used.

2. The salt analyzer of claim 1 wherein said AC voltage source further comprises in series a voltage controlled oscillator, a first programmable gain amplifier and a buffer, the output of which provides the power to drive said probe, said first voltage amplifying means comprises in series a selectable gain preamplifier, a programmable gain amplifier and a full wave rectifier, and said second voltage amplifying means comprises a fixed gain amplifier if a non-contact probe is employed or current amplifying means if a contact probe is employed in series with a full wave rectifier, the output of said first voltage amplifying means comprising V2, and the output of said second voltage amplifying means comprises V1, and wherein said salt analyzer further comprises a calculation means for calculating the salinity of the solution.

3. The salt analyzer of claim 2 wherein said probe is in the contact probe configuration, the selectable gain preamplifier of the first voltage amplifying means is connected across the probe terminals, and said switching means provides current flow from said probe to said second voltage amplifying means which measures a voltage corresponding to the current through said contact probe.

4. The salt analyzer of claim 2 wherein said probe is in the non-contact probe configuration, the sense winding of said non-contact probe is connected to said first voltage amplifying means to obtain V2, and wherein the output of the voltage controlled oscillator of said AC voltage source is also fed to said second voltage amplifying means to obtain VI.

5. The salt analyzer of claim 2 wherein the drive frequency provided by said AC voltage source is determined by the voltage controlled oscillator, said drive frequency being 5.8 KHz for the non-contact probe configuration and 12 KHz for the contact probe configuration.

6. The salt analyzer of claim 2 wherein the salinity of said liquid solution is calculated by said calculation means by first calculating the conductivity of the solution at the cell temperature of the solution in accordance with the formula:

$$K_T = \frac{G_S}{G_A} \frac{V_1}{V_2} C_C \text{ (mS/cm)}$$

for contact probes and $$K_T = \frac{500}{G_S G_P} \frac{V_2}{V_1} C_C \text{ (mS/cm)}$$

for non-contact probes wherein
$K_T$ = conductivity in milli Siemens/cm (mS/cm)
$G_P$ = gain of first programmable gain amplifier (12),
$G_A$ = gain of current amplifier (22), and
$G_S$ = gain of second programmable gain amplifier (20);
$C_C$ = cell constant;
then calculating the conductivity (K) at the standard temperature of 20° C. in accordance with the formula:

$$K = K_T/(0.61047 + 1.8409(10^{-2})T + 5.8044(10^{-5})T^2),$$

where
T = temperature (°C.) of the solution in the cell; and then calculating salinity.

* * * * *

UNITED STATES PATENT AND TRADEMARK OFFICE
CERTIFICATE OF CORRECTION

PATENT NO. : 5,266,899

DATED : November 30, 1993

INVENTOR(S) : BULL, Rame W. et al.

It is certified that error appears in the above—identified patent and that said Letters Patent is hereby corrected as shown below:

Col. 6, claim 4, line 9, change "VI" to --V1--.

Signed and Sealed this

Twenty-sixth Day of July, 1994

Attest:

BRUCE LEHMAN

Attesting Officer  Commissioner of Patents and Trademarks